(12) United States Patent
Calderón

(10) Patent No.: US 9,072,574 B2
(45) Date of Patent: Jul. 7, 2015

(54) PERIOSTEAL ELEVATOR AND IMPLANT SPACING INSTRUMENT

(71) Applicant: Mike E. Calderón, Freeport, NY (US)

(72) Inventor: Mike E. Calderón, Freeport, NY (US)

(*) Notice: Subject to any disclaimer, the term of this patent is extended or adjusted under 35 U.S.C. 154(b) by 1 day.

(21) Appl. No.: 13/945,190

(22) Filed: Jul. 18, 2013

(65) Prior Publication Data

US 2015/0024339 A1    Jan. 22, 2015

(51) Int. Cl.
*A61C 19/00* (2006.01)
*A61C 19/04* (2006.01)
*A61C 8/00* (2006.01)

(52) U.S. Cl.
CPC ............. *A61C 19/04* (2013.01); *A61C 8/0089* (2013.01)

(58) Field of Classification Search
CPC .... A61C 19/04; A61C 19/043; A61C 8/0089; A61C 8/0092
USPC ............... 433/141, 143, 144, 72, 75
See application file for complete search history.

(56) References Cited

U.S. PATENT DOCUMENTS

| | | | | |
|---|---|---|---|---|
| 575,750 | A * | 1/1897 | Winkler | 433/143 |
| 1,410,296 | A * | 3/1922 | Hannah | 433/144 |
| 4,060,897 | A * | 12/1977 | Greenstein | 433/144 |
| 4,270,902 | A * | 6/1981 | Wiland | 433/144 |
| 4,832,683 | A | 5/1989 | Idemoto et al. | |
| 4,872,840 | A | 10/1989 | Bori | |
| 5,217,476 | A * | 6/1993 | Wishinsky | 606/167 |
| 5,302,127 | A | 4/1994 | Crisio, Jr. | |
| 5,336,090 | A | 8/1994 | Wilson, Jr. et al. | |
| 5,482,463 | A | 1/1996 | Wilson, Jr. et al. | |
| 5,513,989 | A | 5/1996 | Crisio | |
| 5,993,209 | A | 11/1999 | Matoba et al. | |
| 6,024,564 | A * | 2/2000 | Kesling | 433/72 |
| 6,241,519 | B1 * | 6/2001 | Sedelmayer | 433/72 |
| 6,347,940 | B1 * | 2/2002 | Gordils Wallis | 433/72 |
| 6,379,371 | B1 | 4/2002 | Novak et al. | |
| 6,447,295 | B1 | 9/2002 | Kumar et al. | |
| 6,592,541 | B1 | 7/2003 | Kurwa | |
| 6,610,066 | B2 | 8/2003 | Dinger et al. | |
| 6,893,260 | B2 * | 5/2005 | Barnes et al. | 433/72 |
| 6,939,135 | B2 | 9/2005 | Sapian | |
| 7,163,395 | B2 * | 1/2007 | Chu | 433/72 |
| 7,300,283 | B2 | 11/2007 | Aravena et al. | |
| 8,377,064 | B2 * | 2/2013 | Wallis | 606/86 R |
| 2003/0224330 | A1 | 12/2003 | Aravena et al. | |
| 2005/0095558 | A1 * | 5/2005 | Jones | 433/144 |
| 2006/0263745 | A1 * | 11/2006 | Lasner | 433/144 |
| 2008/0118892 | A1 | 5/2008 | Adams | |
| 2009/0181343 | A1 | 7/2009 | Hernandez et al. | |
| 2012/0231411 | A1 * | 9/2012 | Verronneau | 433/75 |

* cited by examiner

*Primary Examiner* — Ralph Lewis
(74) *Attorney, Agent, or Firm* — Collard & Roe, P.C.

(57) ABSTRACT

A periosteal elevator has a shaft and a head portion connected to the shaft. The head portion has a blade at a distal end for elevating periosteum from a bone during surgery. The head portion has a distal section, a central section and a proximal section, the distal section being wider than the proximal section and the central section being narrower than both the distal section and the proximal section. Measurement markings are placed on each of the distal section, the central section and the proximal section, the markings measuring the width of each of the sections.

8 Claims, 1 Drawing Sheet

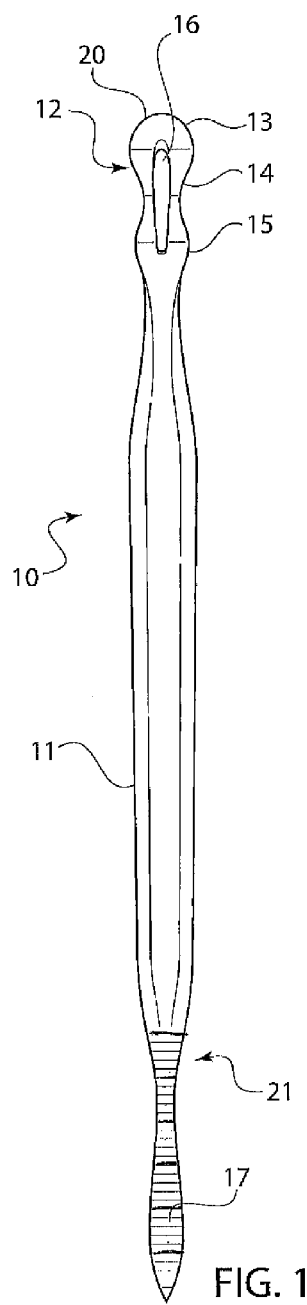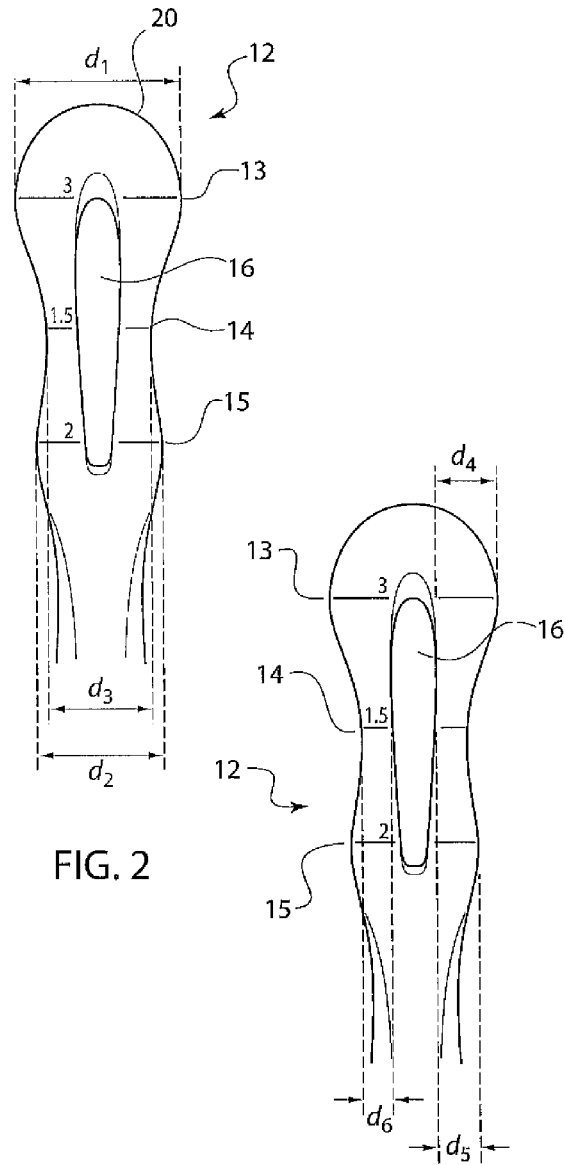
FIG. 1
FIG. 2
FIG. 3

PERIOSTEAL ELEVATOR AND IMPLANT SPACING INSTRUMENT

BACKGROUND OF THE INVENTION

1. Field of the Invention

This invention relates to a periosteal elevator. In particular the invention relates to a periosteal elevator that is also capable of doing measurements for implant spacing during use.

2. The Prior Art

During surgery the dentist often needs to separate a bone or tooth from the fibrous membrane, called the periosteum that covers it. This is done with a periosteal elevator. The dentist may also use it to gain access to retained roots and surrounding bone. Periosteal elevators are commonly used during dental implant surgery. During this implantation process, various measurements need to be taken to ensure that the implant fixture is placed properly into the jaw. In particular, the height of the post, as well as the spacing of the post from adjacent teeth must be measured. These measurements are usually carried out with a specialized measuring tool. However, during the measurement process, the periosteal elevator must be removed from the patient's mouth in order to provide room for the measurement tool. This constant changing of tools is cumbersome and time consuming for the dentist.

SUMMARY OF THE INVENTION

It is therefore an object of the invention to provide a periosteal elevator that is capable of performing all of the measurements necessary for a dental implant process, so that the elevator does not have to be removed from the patient's mouth during the surgery.

This object is accomplished by a periosteal elevator, comprising a shaft having two ends, and a head portion connected to the shaft at one of the ends. The head portion has blade at a distal end for elevating periosteum from a bone during surgery. The other end can form another dental tool such as a scraper for scorring.

The head portion has a distal section, a central section and a proximal section, the distal section being wider than the proximal section and the central section being narrower than both the distal section and the proximal section. Thus, the head portion takes on the shape of a peanut.

Measurement markings are placed on each of the distal section, the central section and the proximal section, the markings measuring the width of each of the sections. Thus, three different ideal measurements can be shown on the head portion.

There is a longitudinal slot cut into the head portion, and extending from the distal portion to the proximal portion. The slot allows suction to be applied through the slot to keep the surgical site dry during bone graft procedures and allows for marking the ideal spacing for the implant osteotomy.

In a preferred embodiment, the slot has a width of approximately 2 mm, the distal portion has a total width of 8 mm, the central portion has a total width of 5 mm and the proximal portion has a total width of 6 mm. This way, the width of the distal portion on each side of the slot is 3 mm, the width of the central section on each side of the slot is 1.5 mm, and the width of the proximal section on each side of the slot is 2 mm.

These measurements are all very useful for various purposes.

For example, 3 mm is the ideal distance from implant surface to implant surface, regardless of the diameter of each implant. The 5 mm width is used as the ideal spacing of a 3.5 mm implant next to a natural tooth. 1.5 mm is the ideal spacing of an implant surface next to a natural tooth. The 6 mm width of the proximal portion is used to position a 4.5 mm implant, as this is the ideal spacing.

The markings preferably extend laterally across a width of the distal section, central section and proximal section. Other variations of the markings could also be used.

Ideally, the end of the shaft is laser etched with 1 mm measurements completely around the circumference of the shaft, from 0 to 30. This allows for quick measurement of connective tissue width, height and thickness. The shaft preferably has a diameter of 8 mm, which is an ideal width for finger positioning and handling of the instrument.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views:

FIG. 1 shows a front view of the periosteal elevator according to the invention;

FIG. 2 shows an enlarged view of the head portion of the periosteal elevator; and FIG. 3 shows another enlarged view of the head portion.

DETAILED DESCRIPTION OF THE PREFERRED EMBODIMENT

Referring now in detail to the drawings, FIG. 1 shows a front view of the periosteal elevator 10. Periosteal elevator 10 comprises a shaft 11 and a head portion 12. Shaft 11 and head portion 12 can be constructed of one piece, or can be separate pieces that are connected together. Head portion 12 has a distal section 13 with a blade 20, a central section 14 and a proximal section 15. A slot 16 is cut longitudinally through head portion 12. The other end of shaft 11 has a scraping tool 17. Shaft 11 preferably has a diameter of approximately 8 mm, with beveled edges, similar to a pencil, to facilitate holding of the instrument.

The end of shaft 11 having scraping tool 17 is marked with 30 1 mm measurement markings 21, to help the surgeon in various measurements. These measurement markings extend around the entire circumference of the elevator 10 and are useful for quick measurement of connective tissue width, height and thickness. Every 5 mm is a physical groove with every 1 mm being laser etched.

In head portion 12, blade 20 is used for lifting the periosteum from the bone or tooth. Slot 16 in head 12 allows quick access of a pilot drill or Thompson stick to mark the area of the osteotomy. It also allows for quick suctioning of heme during the bone grafting procedure. Slot 16 preferably has a width of 2 mm.

As shown in FIG. 2, distal section 13 of shaft 12 has a diameter $d_1$. Diameter $d_1$ is preferably 8 mm. Central section 14 has a diameter $d_3$, which is preferably 5 mm, and proximal section 15 has a diameter $d_2$, which is preferably 6 mm. The 5 mm spacing of $d_3$ of the central section is the ideal spacing of a 3.5 mm implant next to a natural tooth. The total width $d_2$ of 6 mm of proximal section 15 is the ideal spacing of a 4.0 to 4.5 mm implant next to a natural tooth.

As shown in FIG. 3, distal section 13 has a width $d_4$ between slot 16 and the side edge of distal section 13. Slot 16 has a width of preferably 2 mm, so $d_4$ amounts to preferably 3 mm. 3 mm is the ideal distance from implant surface to implant surface, regardless of the implant diameter.

Central section 14 has a width $d_6$, measured from the edge of slot 16 to the edge of central section 14. Width $d_6$ preferably has a width of 1.5 mm. 1.5 mm is the ideal measurement of an implant surface to an adjacent tooth surface.

Proximal section 15 has a width $d_5$, measured from the edge of slot 16 to the edge of proximal section 15. Width $d_5$ is preferably 2 mm.

The measurement markings on the periosteal elevator according to the present invention allow the surgeon to accurately place dental implants without having to remove the elevator from the patient's mouth to do the measurements. This saves a lot of time during surgery.

Accordingly, while only one embodiment of the present invention has been shown and described, it is obvious that many changes and modifications may be made thereunto without departing from the spirit and scope of the invention.

What is claimed is:

1. A periosteal elevator comprising:
a shaft having two ends;
a head portion connected to the shaft at one of the ends, the head portion having a blade at a distal end, said blade being configured for elevating periosteum from a bone during surgery,
wherein the head portion has a distal section, a central section and a proximal section, the distal section having a width that is greater than a width of the proximal section and the central section having a width that is smaller than the widths of both the distal section and the proximal section,
wherein measurement markings are placed on each of the distal section, the central section and the proximal section, the markings measuring the width of each of the sections, and
wherein the head portion has a longitudinal slot extending through a depth of the head portion, the slot bisecting the width of the head portin and having a length extending from the distal section to the proximal section.

2. The periosteal elevator according to claim 1, wherein the slot has a width of approximately 2 mm, the distal section has a total width of 8 mm, the central section has a total width of 5 mm and the proximal section has a total width of 6 mm.

3. The periosteal elevator according to claim 2, wherein the shaft has a diameter of 8 mm.

4. The periosteal elevator according to claim 1, wherein an end of the shaft not connected to the head portion is connected to a scraping tool.

5. The periosteal elevator according to claim 1, wherein an end of the shaft not connected to the head portion has circumferential measurement markings, in 1 mm increments.

6. The periosteal elevator according to claim 1, wherein the markings extend laterally across the width of the distal section, central section and proximal section.

7. The periosteal elevator according to claim 1, wherein the markings indicate the width of each of the sections.

8. The periosteal elevator according to claim 1, wherein the shaft and head portion are constructed of one piece.

* * * * *